United States Patent [19]

Melcher

[11] Patent Number: 5,015,951
[45] Date of Patent: May 14, 1991

[54] APPARATUS AND METHODS FOR MEASURING PERMEABILITY AND CONDUCTIVITY IN MATERIALS USING MULTIPLE WAVENUMBER MAGNETIC INTERROGATIONS

[75] Inventor: James R. Melcher, Lexington, Mass.
[73] Assignee: Massachusetts Institute of Technology, Cambridge, Mass.
[21] Appl. No.: 325,695
[22] Filed: Mar. 20, 1989

Related U.S. Application Data

[63] Continuation-in-part of Ser. No. 104,179, Oct. 2, 1987, Pat. No. 4,814,690.

[51] Int. Cl.$^5$ .................... G01N 27/72; G01R 33/12
[52] U.S. Cl. .................... 324/232; 324/239; 324/243
[58] Field of Search ............ 324/232, 233, 239–243, 324/222, 223, 228, 234

[56] References Cited

U.S. PATENT DOCUMENTS

| | | | |
|---|---|---|---|
| 3,686,564 | 8/1972 | Mallich, Jr. et al. | 324/232 |
| 4,058,766 | 11/1977 | Vogel et al. | 324/61 R |
| 4,399,100 | 8/1983 | Zsolany et al. | 422/62 |
| 4,423,371 | 1/1985 | Senturia et al. | 324/65 |
| 4,496,697 | 1/1985 | Zsolnay et al. | 526/60 |

FOREIGN PATENT DOCUMENTS

| | | | |
|---|---|---|---|
| 0894547 | 12/1981 | U.S.S.R. | 324/232 |
| 1095101 | 5/1984 | U.S.S.R. | |

OTHER PUBLICATIONS

Zaretsky et al., *LEES Technical Report*, pp. 1–43, Jul. 1986.

Primary Examiner—Walter E. Snow
Attorney, Agent, or Firm—Thomas J. Engellenner

[57] ABSTRACT

Devices and analytical techniques are disclosed for measuring spatial profiles of complex permeability and conductivity of a material by multiple wavenumber interrogations. Coil array structures are disclosed which define a number of different fundamental wavelengths (or wavenumbers). Spatially periodic interrogation signals (of temporal frequency "ω") from the coil array structures are attenuated by varying degrees in the material undergoing analysis, depending on the wavenumber ("k"), thereby permitting the derivation of composite complex permeability/conductivity profile.

20 Claims, 6 Drawing Sheets

APPARATUS AND METHODS FOR MEASURING PERMEABILITY AND CONDUCTIVITY IN MATERIALS USING MULTIPLE WAVENUMBER MAGNETIC INTERROGATIONS

REFERENCE TO RELATED APPLICATION

This application is a continuation-in-part of U.S. patent application Ser. No. 104,179 filed Oct. 2, 1987 now U.S. Pat. No. 4,814,690 issued Mar. 21, 1989.

BACKGROUND OF THE INVENTION

The technical field of this invention is magnetometry and, in particular, the spatial interrogation of materials to deduce their physical properties from measurements of complex permeability and conductivity.

Magnetometers or arrays of coils have been used for noninvasive measurement of kinematic and physical properties of conducting materials. For example, eddy current sensors have been used to measure the thickness of conducting strips, as disclosed in Soviet Patents 573,609 and 502,205. Another use of such eddy current sensors has been in flaw detection, as disclosed in U.S. Pat. No. 3,939,404. However, the utility of these sensors typically is limited by their inability to provide enough information to resolve distributions of parameters.

There exists a need for better permeability/conductivity measuring devices and methods. In particular, there exists a need for better devices and methods for conducting non-destructive interrogations of materials to determine their physical properties across a spatial profile.

SUMMARY OF THE INVENTION

Devices and analytical techniques are disclosed for measuring the spatial profile of complex permeability and conductivity of a material by multiple wavenumber interrogations. Coil structures are disclosed which define a number of different fundamental wavelengths (or wavenumbers, k). Spatially periodic interrogation signals (of temporal frequency $\omega$) from the windings of a driver structure are attenuated to varying degrees in the material undergoing analysis. The degree of attenuation depends upon the wavenumber, k, thereby permitting the derivation of a composite profile of complex permeability and conductivity.

The techniques described herein are referred to as an "imposed $\omega$-k" approach to magnetometry. A spatially periodic field is imposed upon the material via a coil structure under the control of a wavenumber controller. The coil structure can be near the material surface or embedded. The properties of the material are reflected in the measurement of the current or voltage induced in the sensing coils in response to this field. By varying the wavenumber, k, a spatial distribution of complex permeability and conductivity is deduced as a function of the temporal frequency, $\omega$, when the property depends only on the coordinate distance, x, perpendicular to the coil structure.

Sensors, according to the present invention, are useful not only in the noninvasive monitoring of the magnetization and conduction properties of materials during manufacturing, but also for measurement of the properties of thin magnetizable films, such as are used for magnetic memories, or for measurement of proximity and/or layer thickness parameters in magnetizable or conductive media.

In one illustrated embodiment, the coil structure consists of an array of superimposed driver windings, designed so that a spatially periodic magnetic field can be imposed on the material over a range of spatial wavelengths, and an array of sensing windings that detect the material response to the fields induced by the driving windings. In another illustrated embodiment, the coil structure is formed from a plurality of different-sized and, hence, different wavelength arrays of meandering driver and sensor coils. In either case, a permeability/conductivity analyzer compares the resulting response sensed by the sensor coil array at different wavenumbers to predictions based on a postulated model in order to derive a spatial profile of the permeability and conductivity of the material.

The invention will next be described in connection with certain illustrated embodiments; however, it should be appreciated that various modifications, additions and subtractions can be made by those skilled in the art without departing from the spirit or scope of the invention. For example, in one illustrated embodiment, the conductor comprising an individual driver coil is distributed so that the current will take on an essentially sinusoidal distribution in space and the capability for multiple wavelength excitation obtained by superimposing these coils in adjacent layers near the surface of the material. These same types of driver coils could be use in an array with coils of different wavelengths at different locations on the surface of the material, as in the second embodiment illustrated. Other types of electromagnetic elements capable of imposing a magnetic field upon a material and sensing a resulting electromagnetic response can also be employed. Yet another modification would be to use the impedance of the driving coils as the sensing variable and dispense with the sensing coils. Moreover, various refinements to the estimation algorithms described below can be incorporated.

DETAILED DESCRIPTION

In conventional magnetometry, the temporal frequency response is used to study the magnetic and electrical attributes of the materials, such as can be discerned through the effect on the fields of molecular and domain-level magnetization and ionic and electronic conduction. In the conventional measurement of complex permeability, a toroid of the material would typically be used. An N turn winding wrapped around the toroid is then driven by a current, $i_1$, and the complex permeability of the material is reflected in the flux linkage, $\lambda_1$. This toroid should have a major radius that is large enough compared to the minor cross-sectional dimensions of the toroid that the fields induced in the material are essentially uniform over the cross-sectional area, A, of the toroid. The response to a sinusoidal drive having the frequency $\omega$ can be defined as the complex inductance $$\hat{L}(\omega) = \frac{\hat{\lambda}_1}{\hat{i}_1} \tag{1}$$

where $\hat{\lambda}_1$ and $\hat{i}_1$ are the complex amplitudes of the flux linkage and current, respectively.

In complex notation, the magnetoquasistatic fields in the material satisfy the magnetic flux continuity law $$\nabla \cdot \hat{\mu}\hat{H} = O \tag{2}$$

where $\mu = \mu(x)$.

The toroid is often used to make the magnetic field permeating the material as uniform as possible. However, the complex permeability, $\mu$, can actually vary with the axial position, x, in the toroid. The effect of the non-uniform permeability is evident in the measured temporal frequency response. Provided that the material is sufficiently insulating that the field due to currents induced in the material are negligible, Ampere's law requires that $$N\hat{i}_1 = \oint_C \hat{H}_x dx \tag{3}$$

where N is the total number of turns and the contour integral is taken in the x direction, around the axis of the toroid.

It follows from Eq. 2 that the product of the magnetic flux density and the cross-sectional area is the same at a location, x, around this closed contour so that $\hat{\lambda}_1 = NA\hat{\mu}\hat{H}_x$ is independent of x Thus, Eq. 3 can be combined with Eq. 1 to give $$N\hat{i}_1 = \oint_C \frac{\hat{\lambda}_1 dx}{NA\hat{\mu}(x)} = \frac{\hat{L}\hat{i}_1}{NA} \oint_C \frac{dx}{\hat{\mu}(x)} \tag{4}$$

and it follows that the measured complex inductance is related to the distribution of complex permeability by $$\hat{L}(\omega) = N^2 A \left[ \oint_C \frac{dx}{\hat{\mu}(x)} \right]^{-1} \tag{5}$$

Measurement of $\hat{L}(\omega)$ at a single temporal frequency therefore gives at best a spatial average of the complex permeability. With assumptions concerning the frequency dependence of the local complex permeability, it is possible to use the full temporal frequency response to distinguish between certain attributes of the non-uniformity. However, the necessity for making assumptions of this type strongly limits what additional information can be obtained concerning the physical mechanisms underlying the complex permeability (such as domain scale dynamics).

Moreover, even with these assumptions, there is no unique relationship between the actual spatial distribution of complex permeability and the temporal frequency response. This follows from Eq. 5 which makes it evident that at a given frequency there are many different distributions giving rise to the same complex inductance. Contributions to the integral coming from the neighborhood at $x=a$ can be interchanged with those at $x=b$ (where a and b are any pair of values), and the integral will be the same. Hence, there can be no unique inference of the spatial distribution from the temporal frequency response alone.

In the present invention, devices and methods are disclosed for using the spatial frequency response (the response as a function of the dominant wavenumber k) to deduce the spatial distribution of complex permeability and/or conductivity (as a function of temporal frequency, $\omega$) when that property depends only on the coordinate, x, perpendicular to the coil-array structure.

This approach exploits a property of magnetoquasistatic fields. If the fields are made to be periodic in one direction, y (the direction of periodicity in the plane of a coil array), they decay in the perpendicular direction, x. If the material is not significantly conducting, this decay in the perpendicular direction, x, is at a rate that is inversely proportional to the wavelength, $\lambda = 2\pi/k$. If the effect of conductivity is important, they decay even more rapidly.

Thus, if a spatially periodic array of coils is used to impose a current and sense the resulting magnetic flux linkage induced in the sensing coil array, the response to the short wavelengths will reflect the permeability and conductivity of the material in the immediate vicinity of the coil-array. The longer-wave coil arrays will not only sample the properties of the immediately adjacent material but those further into the material as well. As the wavelength is further increased, the permeability and conductivity at an increasing range from the sensing surface will influence the measurement. In the case where the material is highly conducting, the depth of penetration and hence of sensitivity will be limited to approximately the skin depth $d=\sqrt{2/\omega\mu\sigma}$ where $\sigma$ is the electrical conductivity. Disclosed in the following is apparatus and method for efficiently reconstructing the permeability/conductivity profile from measurements made as a function of wavenumber (wavelength).

Figure 1:
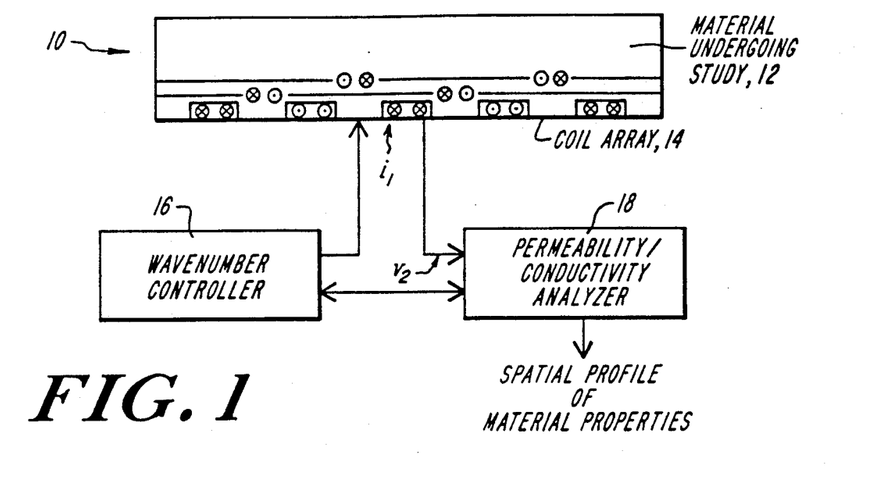
FIG. 1 is an overall schematic diagram of a permeability/conductivity analyzing apparatus according to the present invention.

In one "imposed $\omega$-k" magnetometry apparatus 10 shown in FIG. 1, a spatially periodic field is imposed on a material 12 by means of an array of coils 14 at the surface of the material. The coil array can be formed on layers of insulating material initially coated by conducting material with the conducting path fabricated by etching away the undesired conductor. The sample 12, which in general is non-uniform in the direction, x, perpendicular to the array is shown just above the coil array. In the apparatus shown, a subset of the coils is driven with the temporally sinusoidally varying current, $i_1$ by wavenumber controller 16 while another subset is connected to high-impedance electronics of the permeability/conductivity analyzer 18 that measures the voltage $v_2$, at the terminals of the sensing coil arrays. For example the analyzer 18 can be a microcomputer programmed to measure the permeability/conductivity of the material at multiple wavelengths based upon a parametric model of the material and perform interactive analyses to obtain a refined spatial profile.

Figure 2:
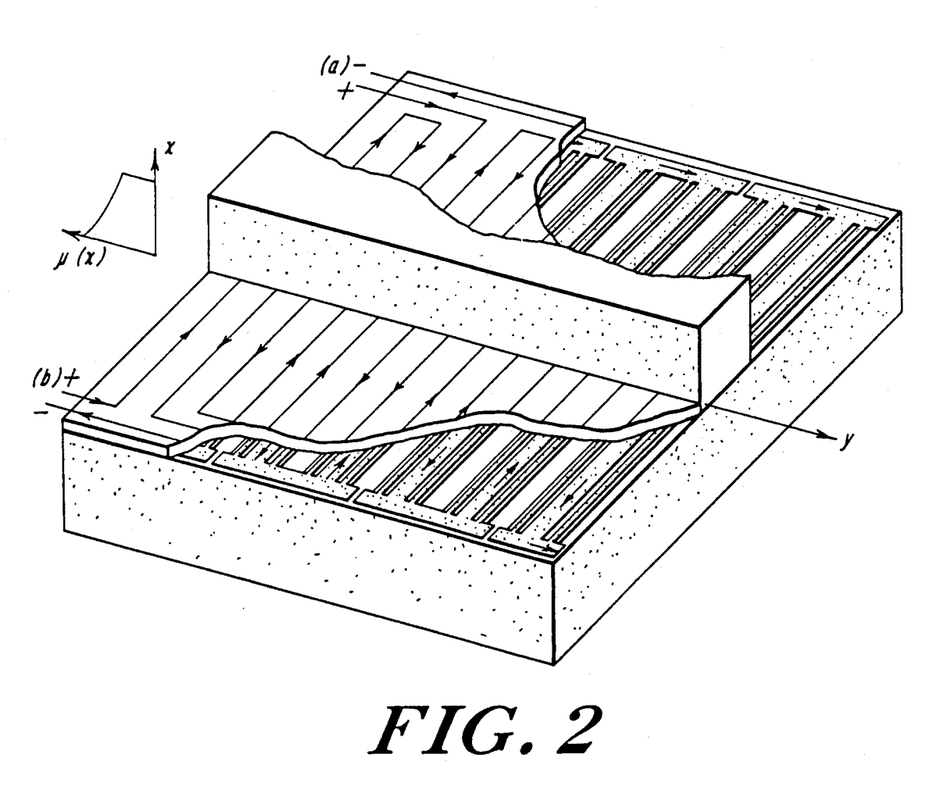
FIG. 2 is a partially cut-away, perspective view of a layer of material having a non-uniform distribution of permeability and/or conductivity in the x direction showing an embodiment of the invention employing superimposed driver and sensor coil windings.
Figure 3:
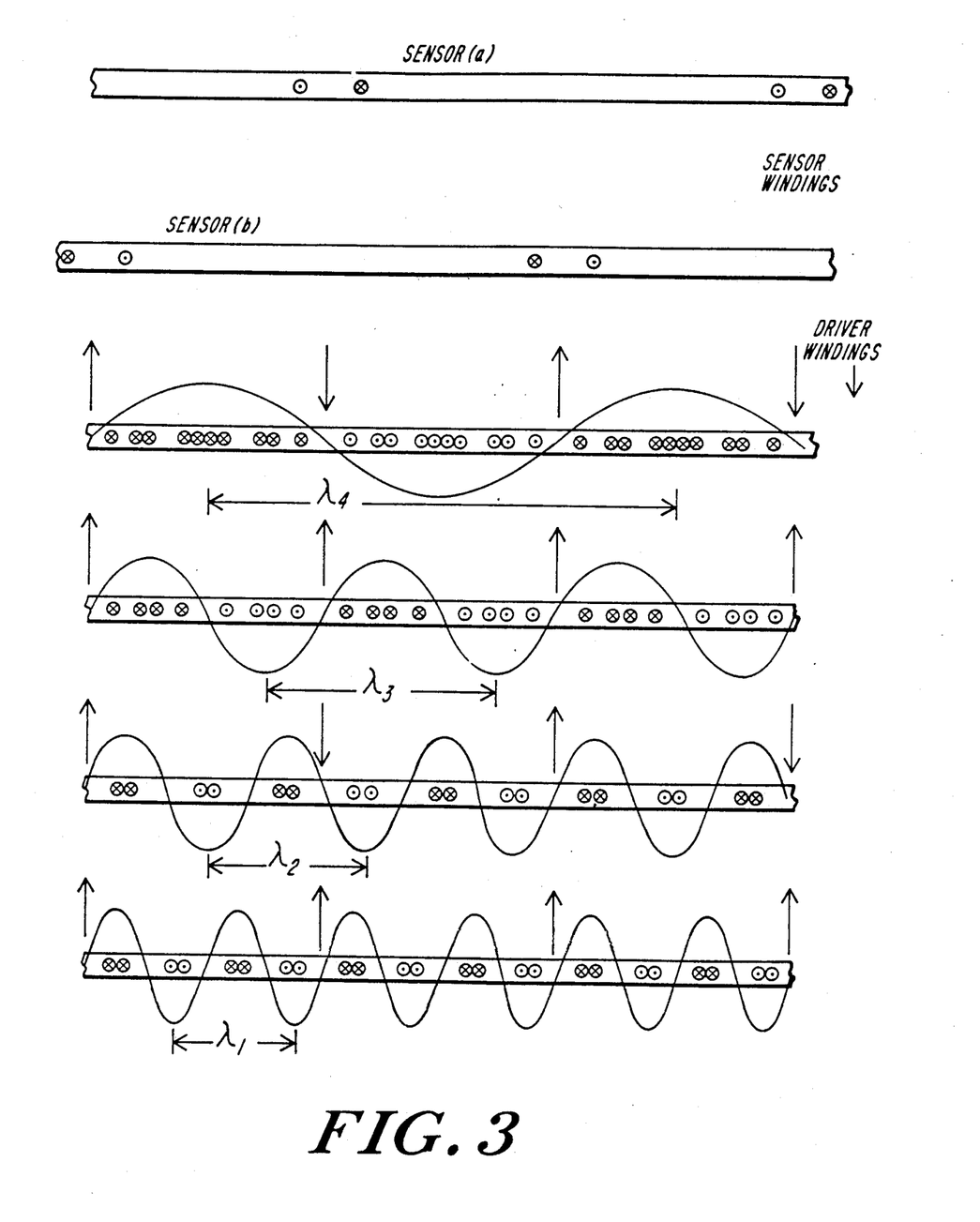
FIG. 3 is a schematic side view of a further apparatus according to the invention illustrating two sensor winding arrays, and four driver winding arrays.
Figure 4:
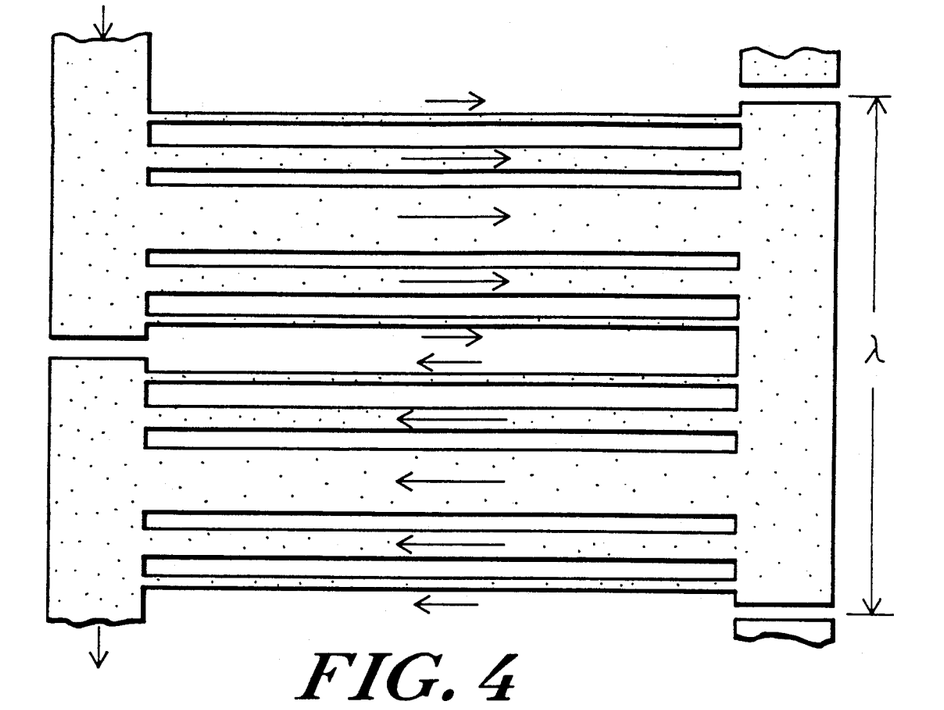
FIG. 4 is a top view of a uniform thickness layer of copper which can be used to make a driver winding array to impose a distribution of current that is approximately sinusoidal in spatial distribution.
Figure 5:
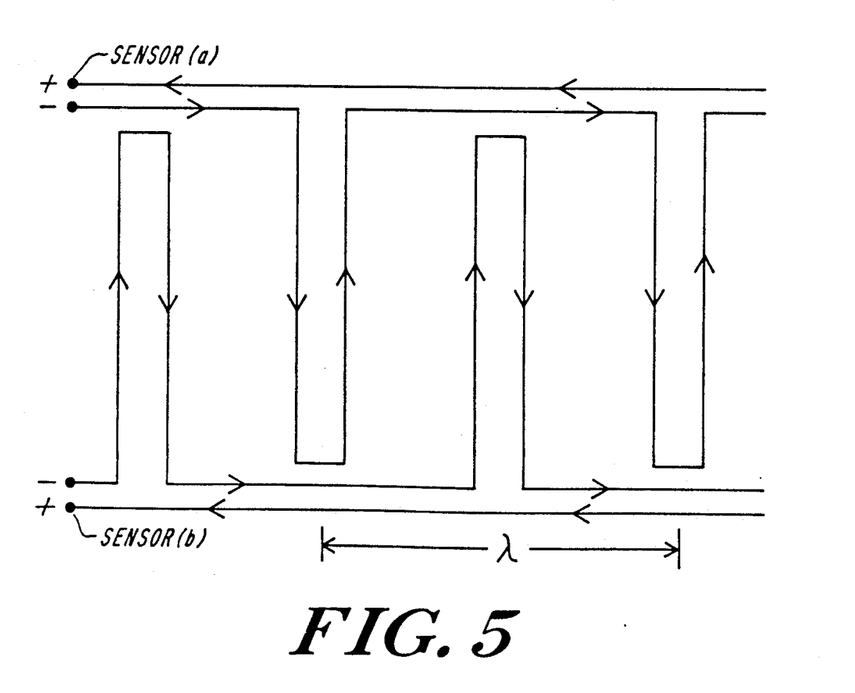
FIG. 5 is a top view of the (a) sensor and (b) sensor winding arrays shown in FIG. 3.

A coil array system which can be conveniently constructed from layers of arrays, each fabricated with conductors on a single surface of an insulator and in which the wavelength is varied by terminal connections that shift the excitation current from one driving array to another is shown in FIG. 2. An edge view of the sensing and driving coil arrays is shown in FIG. 3. It should be noted that the sensor arrays (a) and (b) of FIG. 3 are illustrated as separate layers stacked one upon the other, however, it should be clear that this arrangement is the equivalent of the coplanar array configurations shown in FIGS. 2 and 5 and can be used interchangeably therewith. In this example, there are two sensing coil arrays, respectively designated as the (a) and (b) sensor windings, and four driver coil windings. Top views of one of the driving arrays and of the sensor array are respectively shown in FIG. 4 and FIG. 5.

The manner in which these arrays can be layered, with the windings insulated from each other by the insulation that serves as a backing for the array just above, is illustrated by FIG. 2, where the two sensor windings and one of the four driver windings is shown. In some applications, it will be preferable to have the short-wavelength driver coil be the driver coil closest to the material although, provided the array layers are thin compared to the shortest wavelength, the shortest wavelength driver coil array could be the furthest from the material, as shown in FIG. 3. In this six layer system, there are four wavelengths that can be obtained by appropriate connection of the driver coil array terminals to the driving current, $i_1$. The (a) and (b) sensor coils are respectively arrayed in series, but with relative polarities such that the signal induced in the (a) array terminals reinforces that induced in the (b) array terminals. From the magnetic axes excited by the driving coils arrays, indicated by the vertical arrows in FIG. 3, it follows that the relative polarity of the series connection of the sensor arrays must be reversed with each increase in the wavelength. At the expense of halving the output voltage, this switching of the output terminal connections can be avoided by eliminating either the (a) or the (b) sensor coil array. With a further reduction in sensor voltage, the single sensor array could be replaced by a smaller number of coils, with the minimum being one.

Figure 6:
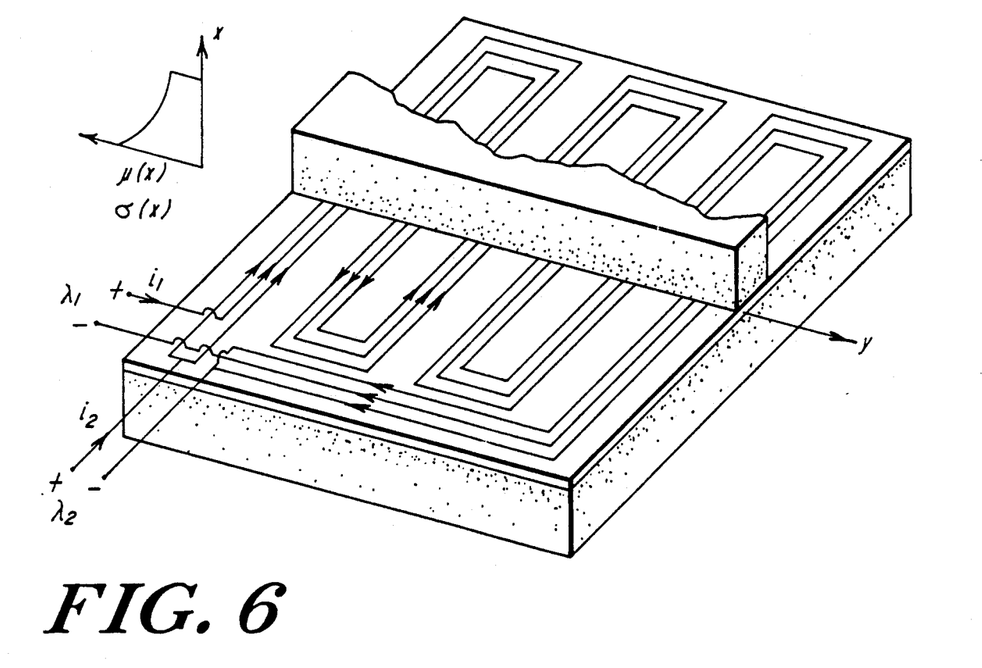
FIG. 6 is a partially cut-away, perspective view of a layer of material having a non-uniform distribution of permeability/conductivity in the x direction showing another embodiment of the invention in which meandering sensor and driver coil arrays are disposed at different positions on the lower surface of the material.
Figure 7:
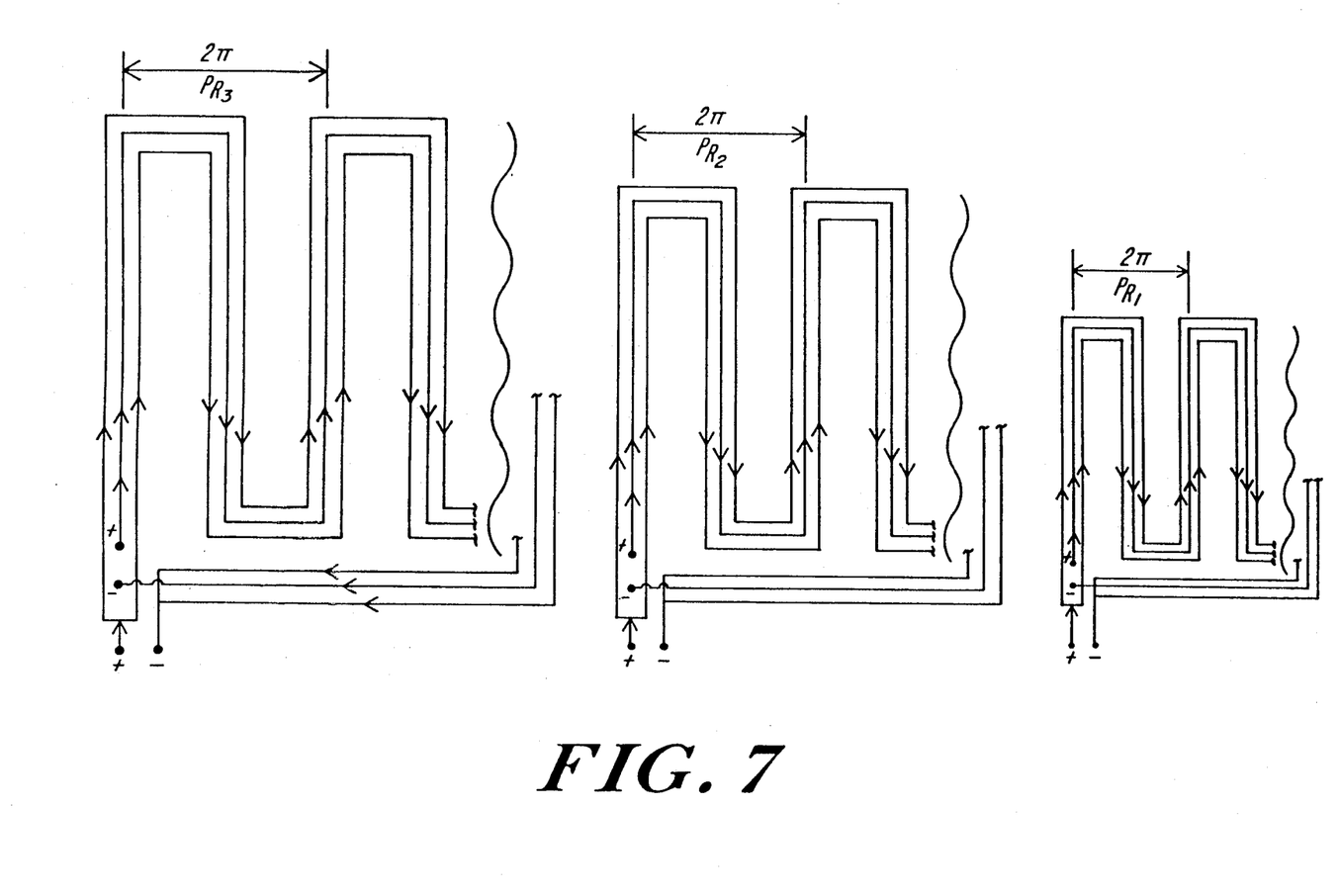
FIG. 7 is a top view illustrating three meandering sensor and driver coil arrays disposed at different positions on the surface of the material.

An alternative embodiment is shown in FIG. 6 and FIG. 7, where the coil array consists of a set of different-sized meandering coil arrays. Illustrated in FIG. 7 is an array having three different wavelengths. Provided the sample facing the coil array has the same permeability/conductivity profile, measurements taken from each can be consistently combined to provide the desired profile. Measurements of the response of the coil array define the gain G, which in general is a complex quantity reflecting both the magnitude and phase of the response. In the case shown in FIG. 1, the gain might be defined as $\hat{v}_2/i_1$. The data to be used in determining the distribution of complex permeability/conductivity consists of a set of gains, $G = G_m$, measured at the dominant wavenumber $k_j$, $j = 1 \ldots N$.

$$G_{measured} = G_m(\omega, k_j), k = k_1 \ldots k_N \quad (6)$$

The dominant wavenumbers are related to the wavelength or periodicity length, $\lambda_j$, by $$k_j = 2\pi/\lambda_j \quad (7)$$

The wavelength is illustrated by FIG. 3. In the following, the data designated by the subscript, j, is taken as being in the order of increasing wavelength and, hence, decreasing wavenumber.

Various representations of the complex permeability/conductivity distributions can be used. For example, the distributions can be represented by layers, each having uniform properties. Alternatively, each layer can have an exponential distribution. Included in each representation is the possibility of having complex surface properties and conductivity at one or more of the interfaces. Without the complex surface properties, the representations approximate the distribution by "stair-step" and piece-wise continuous functions, respectively.

The "direct problem" is the basis for inferring the distribution from the data. Here, the object is to predict the gain, given the distribution of permeability/conductivity. To prevent errors in deducing the distribution that are associated with the geometry of the coil array, it is desirable to have a method of solving the direct problem that takes the finite width and spacing of the coil conductors, as well as the properties of their substrate, into account. This is especially true if, as to be described next, the inversion procedure "marches" from short to long-wave lengths. Although finite difference and finite element numerical methods can be used to take into account the effects of geometry, a collocation technique based on a spatial Fourier decomposition of the fields has been shown to be well suited to the direct problem. At very low frequencies where the current density is uniformly distributed in the driver and sensor conductors, the Fourier decomposition can be carried out without requiring the collocation technique.

Using the Fourier decomposition approach at higher frequencies, the mixed boundary value problem posed where the coil array interfaces the media is solved by representing the distribution of the surface current density within the coil conductors, or alternatively the vectors potential distribution within and between the coil conductors by a piece-wise continuous surface current density and vector potential having collocation values $K_j$ and $A_j$, where the distributions are respectively pieced together.

Given the distribution of material properties, the specific surface inductance density, $L_n$ can be predicted. This is the complex normal magnetic flux density response of the media (at the plane of its interface with the coil array structure) to a complex magnetic scalar potential in that plane having a purely sinusoidal spatial distribution with wavenumber $k_n$ and purely sinusoidal time variation, with angular frequency $\omega$. The fields above the coil array and at the interface between the coil conductors are also represented by their spatial Fourier components. These fields are then made self-consistent with those in the media by a numerical evaluation of the collocation surface, current densities, $K_j$, and vector potentials, $A_j$, making it possible to evaluate the admittances in the circuit. These admittances represent the response with arbitrary types of termination.

For the particular case where the gain is defined as the complex ratio of the output voltage to driving current, where $\hat{Y}_{11}$, $\hat{Y}_{12}$, $\hat{Y}_{21}$, and $\hat{Y}_{22}$ are the admittances of a standard two-port network representing the combination of coil array and media subject to measurement, $$G = \frac{\hat{V}_2}{\hat{i}_1} = \frac{\hat{y}_{21}}{\hat{y}_{12}\hat{y}_{21} - \hat{y}_{11}\hat{y}_{22}} \quad (8)$$

The same circuit elements can be used to predict the driven impedance or the sensor response when the sensing coils are terminated in an arbitrary impedance.

Inversion methods build on having the capability for solving a family of direct problems. Inversion methods must deduce the discrete properties needed to complete the representation from the available discrete gain measurements made over an appropriate range of imposed dominant wavelengths. These are the gain measurement summarized by Eq. 6. In general, N gains are measured ranging over wavelengths short enough to resolve the distribution close to the array and ending at a wavelength long enough to make the field extend far enough into the material to reflect material properties to the desired depth. With properly designed coils and material properties that do not suffer extreme variations, profiles are sensed to a depth that is approximately a quarter wavelength. In general, the inversion method then provides for an identification of N parameters describing the permeability/conductivity distribution from these N measurements. In the case of a stair-step approximation, the distribution of complex permeability/conductivity would be represented by the N complex permeabilities/conductivities of the steps. In the case where (perhaps exponential) functions are pieced together in a continuous manner, the N identified permeabilities/conductivities could be those at the locations where the smooth distribution is pieced together. In any case, the introduction of complex surface permeabilities/conductivities imposes a requirement for additional data. Thus, with N measurements over an appropriate range of wavelengths, it would be possible to deduce N-S bulk parameters describing either the stair-step or the piece-wise distributions and S complex surface permeabilities/conductivities.

It is important to note that the inversion process can be carried out using measurements taken at the same frequency. Thus, the permeability/conductivity distributions can be deduced at each frequency. The information inherent to the temporal frequency response is therefore preserved and can be exploited for further parameter identification purposes.

The estimation of parameters from experimental data can be formalized by defining an error that is the difference between the measured gains and those predicted by the direct method $$e = G_{measured} - G(\theta)_{predicted} \quad (9)$$

Here, $\theta$ is a list or one or more parameters to be estimated and e is a column vector of errors associated with the different gains.

If, as in the illustration used here, there are as many measured gains as parameters to be determined, the estimation process then amounts to finding those values of $\theta$ that make $$e(\theta) = 0 \quad (10)$$

If there are more measurements than parameters so that the identification problem is overspecified, the estimation process can be represented as a minimization of a quadratic norm based on these errors and possibly a weighting function.

Figure 8:
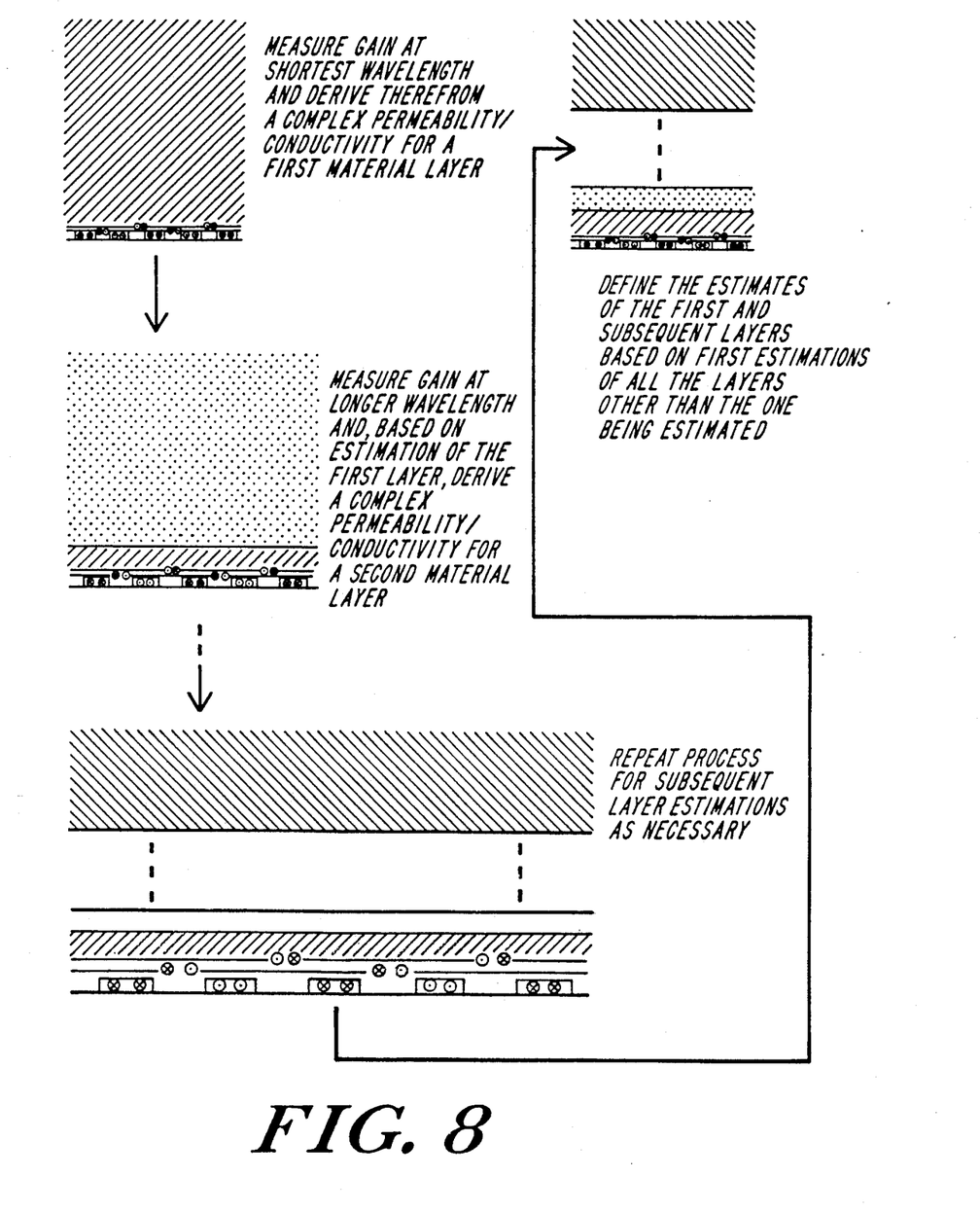
FIG. 8 is a flow diagram of a permeability/conductivity analyzer according to the present invention.

As shown in FIG. 8, in one algorithm, the estimation problem can be reduced to a sequence of single parameter estimations (or perhaps two parameter estimations) by again exploiting the properties of quasistatic fields. For example, suppose the inhomogeneity is smooth. Then, the gain $G_m(k_1)$ measured at the shortest wavelength is used in conjunction with a single layer model to deduce the complex permeability/conductivity of the material nearest to the coil arrays. With this in hand, the complex permeability/conductivity of the material somewhat further out is determined from the gain $G_m(k_2)$ measured at the next longer wavelength. Like the first step, this one amounts to a single parameter estimation of the complex permeability/conductivity of the second layer in a two-layer model for the media. Following this procedure, the measured gain $G_m(k_j)$ is used in conjunction with a model representing the complex permeability/conductivity by j parameters, the last of which is associated with the layer furthest from the coil array (and about a quarter wavelength from the coil array, based on the wavenumber of that measurement) to make a single parameter estimation. Once the first pass has been made through the data, working from short to long wavelengths and, hence, performing a sequence of single parameter estimations of the profile working outward from the coil arrays, the parameters can be refined by passing through the data, again from short to long wavelengths. In these subsequent iterations, the parameters of layers other than the one being estimated are taken as being their values on the last estimation.

An optimal parameter estimation scheme takes advantage of all a priori knowledge of the complex permeability/conductivity distribution. For example, if it is known that the material actually consists of one or more discrete layers across the boundaries of which it is expected that the complex permeability/conductivity suffers an abrupt change, then a model can be used in which one or more of the layers represent the boundaries between actual physical layers. If the locations of such abrupt changes are not known, the parameter estimation scheme can then be one in which the location of such a boundary is one of the parameters being estimated. In some instances, the inversion can best be reduced to one or perhaps a sequence of multiple parameter estimations. For one skilled in the art, the single parameter estimation techniques described herein are readily generalized to the simultaneous estimation of multiple parameters.

What is claimed is:

1. An apparatus for measuring a property of a material, the apparatus comprising:

an array of electromagnetic elements capable of imposing a magnetic field in a material and sensing a resulting electromagnetic response;

a wavenumber controller connected to said array for applying a current to subsets of said electromagnetic elements and thereby defining fundamental wavenumbers associated with said imposed magnetic field in the material; and an analyzer connected to said wavenumber controller, including means for comparing the resulting responses sensed by said electromagnetic array at different wavenumbers to predictions in order to derive a spatial profile of complex permeability or conductivity in the material.

2. The apparatus of claim 1 wherein the electromagnetic array comprises a plurality of electrically-driven layered coils.

3. The apparatus of claim 1 wherein the electromagnetic array comprises a plurality of layered coil arrays having conduction paths distributed so as to approximate a sinusoidal distribution.

4. The apparatus of claim 1 wherein the electromagnetic array further comprises a plurality of driver coil arrays and at least one sensor coil array, the driver coil arrays each having a different wavelength and each disposed at a different location on the surface of the material.

5. The apparatus of claim 4 wherein the sensing array of coils comprises a plurality of layered coil arrays capable of sensing the flux induced at the surface of the material at a plurality of wavelengths.

6. The apparatus of claim 4 wherein the electromagnetic array further comprises a plurality of coil elements formed as intermeandering conductors.

7. The apparatus of claim 4 wherein the wavenumber controller further comprises electronic switches for applying one current to the appropriate driver coil array.

8. The apparatus of claim 4 wherein the wavenumber controller further comprises means for connecting the terminals of the sensor coil array or arrays so that a signal is detected at the wavelength that is the same as that of a corresponding the driver coil array.

9. The apparatus of claim 1 wherein the permeability/conductivity analyzer is a microcomputer programmed to measure the permeability/conductivity of the material at multiple wavelengths based upon a parametric model of the material and further includes means for performing interactive analyses to obtain a refined spatial profile.

10. A method for measuring the properties of a material, the method comprising:
disposing an array of electromagnetic elements in proximity to a material, the electromagnetic elements being adapted to impose a magnetic field in the material and sense a resulting electromagnetic response;
interrogating the material with a magnetic field at multiple wavelengths defines by subsets of said electromagnetic elements;
sensing the resulting electromagnetic response at multiple wavelengths; and deriving a spatial profile of at least one property of the material from said electromagnetic response.

11. The method of claim 10 wherein the step of interrogating the material further includes sequentially interrogating the material at multiple wavelengths.

12. The method of claim 10 wherein the step of interrogating the material further includes simultaneously interrogating the material at multiple wavelengths.

13. A method for measuring the properties of a material, the method comprising:
disposing an array of electromagnetic elements in proximity to a material, the electromagnetic elements being adapted to impose a magnetic field in the material and sense a resulting electromagnetic response;
interrogating the material with a magnetic field at multiple wavelengths defined by subsets of said electromagnetic elements;
sensing the resulting electromagnetic response at multiple wavelengths to derive a spatial profile of at least one property of the material;
measuring the gain at the shortest wavelength to derive a profile estimation for a first material layer; and
measuring the gain with at least one longer wavelength to derive a profile estimation for a subsequent material layer.

14. The method of claim 13 wherein the method further includes employing a parametric model to obtain said estimations for the first and subsequent material layers.

15. The method of claim 13 wherein a linear model is employed to represent the layers.

16. The method of claim 13 wherein an exponential model is employed to represent the layers.

17. The method of claim 13 wherein a continuous model is employed to represent the layers.

18. The method of claim 13 wherein a step function model is employed to represent the layers.

19. The method of claim 13 wherein the method further includes refining the estimate of each layer based on a prior estimation of all the layers other than the one being refined.

20. The method of claim 18 wherein the step of refining the estimate is iteratively repeated for each layer until a best fit to a parametric model is obtained.

* * * * *